United States Patent [19]

Bendel et al.

[11] Patent Number: 5,000,912
[45] Date of Patent: Mar. 19, 1991

[54] NICKEL TITANIUM MARTENSITIC STEEL FOR SURGICAL NEEDLES

[75] Inventors: Lee P. Bendel, Lebanon; Timothy A. Sardelis, Somerset, both of N.J.

[73] Assignee: Ethicon, Inc., Somerville, N.J.

[21] Appl. No.: 451,078

[22] Filed: Dec. 15, 1989

[51] Int. Cl.$^5$ .................... C22C 38/44; C22C 39/20; C21D 7/02

[52] U.S. Cl. .................... 420/34; 148/12 E; 148/325; 148/326; 420/57; 420/48; 420/52; 420/67; 420/68

[58] Field of Search .............. 420/34, 37, 48, 67, 420/52, 68; 148/12 E, 325, 326

[56] References Cited

U.S. PATENT DOCUMENTS

| | | | |
|---|---|---|---|
| 3,769,003 | 10/1973 | Kenyon | 420/67 |
| 3,925,064 | 12/1975 | Takamura et al. | 420/68 |
| 4,740,353 | 4/1988 | Cogan et al. | 420/52 |
| 4,775,426 | 10/1988 | Murley et al. | 148/12 E |

OTHER PUBLICATIONS

"Martensite" ed E. R. Petty, Longman, Bristol, 1970, pp. 161–176; 183–186.

*Primary Examiner*—Upendra Roy
*Attorney, Agent, or Firm*—Paul A. Coletti

[57] ABSTRACT

A needle alloy wherein the nickel content is between 6.3% and 9.5%, the chromium content is between 11.5% and 12.5% and the molydenum content is between 3% and 4%. In addition, tantalum and titanium should be present at a combined level of no more than 2.1%. Favorable results from this alloy cause needles to have a greater than 400,000 psi ultimate tensile strength.

26 Claims, No Drawings

NICKEL TITANIUM MARTENSITIC STEEL FOR SURGICAL NEEDLES

THE FIELD OF THE INVENTION

Generally, this invention relates to the field of steel alloys. More specifically, the alloy of the invention relates to work hardenable, maraged stainless steel. Most specifically, the alloy in this invention relates to a material used in surgical needles formed from work hardenable, maraged stainless steel.

BACKGROUND OF THE INVENTION

Presently, many types of alloys are used in the production of surgical needles Some such alloys are martensitic stainless steels, austenitic stainless steels, and plated plain carbon steel. These alloys range from materials which exhibit acceptable characteristics regarding corrosion resistance, strength and ductility. Of course, primary among all these factors is strength. Naturally, the ultimate tensile strength of an alloy is ideally as high as possible for manufacture, while not compromising any of the other characteristics of the material. The ultimate tensile strength of the precipitation grade steel can be described as a combination of an annealed strength added to a work hardening response, which is aged hardened. In general, it is desirable for current chemistries from which needles are formed to have an ultimate tensile strength greater than 400,000 pounds per square inch (400 ksi).

In general, the alloys on which this application focuses are called maraging stainless steels. This terminology indicates hardening by martensitic transformation, with precipitation hardened by aging. Stainless steel means a relatively high chromium level in the alloy, usually 12 percent or greater.

The first stage in processing these steels is annealing, or solution treatment. This entails heating the material to a suitable temperature (between 1500° F. and 2100° F.), sufficiently long to place one or more constituent elements into solid solution in the base metal. More preferably, maraged steels are solution treated between 1980° F. and 2080° F. The phase change of the solution from an austenitic state to its martensitic state commonly occurs in these alloys during cooling from the elevated temperature of the solution treatment. A rapid cooling rate insures that constituents remain in super saturated solid solution, also avoiding unwanted precipitation that might occur during a slow cool. The transformation to martensite is therefore a diffusionless phase change. Alloy additions remained trapped in solution within resulting martensite, filling interstitial sites of the base metal. In this regard, the additions block dislocation propagation and further strain the structural lattice of the alloy. Certain alloy additions may also cause martensite refinement, thus hardening or toughening the alloy due to finer martensite plate spacing.

Next, the alloy is work hardened to gain additional strength. Work hardening is a process which increases the strength of a metal by the addition of mechanical deformation. Any process that increases the resistance to slip or the motion of dislocations in the lattice structure of crystals will increase the strength of the material. In work hardening this resistance is caused by immobile obstacles generated during the deformation process itself. They can be arrays of other dislocations or grain boundaries, the number of which is also increased by the mechanical work.

Finally, precipitation or age hardening is accomplished by aging the alloy at intermediate temperatures, high enough to reactivate both diffusion and the formation of intermetallic compounds. Generally age hardening occurs between temperatures of 750° F. to 1050° F. Preferably maraged steels are precipitation hardened between about 825° F. and 975° F. A dispersion of fine precipitates nucleate at dislocations and at martensite plate boundaries, resulting in further hardening of the alloy.

Balancing ultimate tensile strength with corrosion resistance and ductility in the maraged steel is difficult to arrange. Many attempts yield high tensile strengths and yet low corrosion resistance, or low ductility. Ultimately therefore, it is the goal of this alloy to balance these criteria, and to produce a strong, ductile and corrosion resistant alloy.

SUMMARY OF THE INVENTION

It is therefore an object of the invention to provide an alloy material which should have not less than 380 ksi yield strength after full processing. The yield bending moments of needles made from this material also should be greater than that of existing needles. For example, for 0.012" diameter needles fabricated out of the subject alloy, an increase of 28% bend strength was found, compared to needles made from alloys currently in use.

The alloy of the invention must also be capable of passing standard corrosion tests, commonly as those described in Federal Specification GG-S-0816c. The materials also should be able to resist corrosion when subjected to 94% relative humidity at 176° F. for up to 100 hours.

It is further an object of the invention to form needles from this alloy which must be able to withstand the bending test described in Federal Specification GG-S-00816c.

It is expected that a minimum of 10.5% chromium is necessary to provide strong corrosion resistance. The maximum chromium level is expected to be about 18%, because it is a strong ferrite former at low nickel levels and a very strong austenite stabilizer at higher nickel levels. It should be noted that it is desirous to have the entire alloy convert from austenitic phase to martensitic phase during solution treatment. Some of the other elements to be added form intermetallic compounds with chromium. The amount of chromium remaining in a nickel matrix should exceed about 10.5% after age hardening.

It is also expected that nickel is required to provide an austenitic structure at temperatures of about 800° C. to 1100° C., which can transform to metastable martensite upon cooling to room temperature. The nickel content required for this function is to be expected in the range of about 4% to about 20%. Nickel must also be present to form a sufficient volume fraction of the various hardening phases of the alloy. The nickel required for this function is expected to be about 6% to about 12%.

Additional to the chromium and nickel content would be other elements such as aluminum, cobalt, molybdenum, niobium, tantalum, titanium, vanadium and tungsten. These elements could possibly be added primarily because of their influence on age hardening response and work hardening rate.

With these criteria in mind, it has been found that the present invention exhibits greatest tensile strength when having the following chemistries. The alloy is an iron base material in which the chromium content varies from about 11½% to about 12½% by weight. Nickel content should be no less than about 6.3% and range no higher than about 9.5%. For a benchmark in the chemistry, it has been found that the total of nickel and chromium should add to about 21%. Any combination of titanium and tantalum should be at least 1.5% and no higher than about 2.1%. Titanium alone, at about 2% by weight, results in a desirable configuration of the alloy. Molybdenum should exist in the alloy at about 3.0% with a maximum of about 4.0%. The remainder of the alloy is iron, with trace elements (no more than 0.1% of sulphur, carbon, oxygen, nitrogen, phosphorous, silicon and manganese.

For further benchmark purposes, it is useful to talk of austenitic retention in the alloy. Previous alloys have been discussed by the amount of austenite remaining after drawing the alloy. The resulting alloy, therefore, possesses an Austenite Retention Index (ARI) of between 17.3 to about 21.4. Present common needle alloys are above this range and have good index retention based on the amount of cobalt they contain. Yet, these properties are accomplished in an alloy where there is virtually no cobalt. It is in the combination of nickel and chromium, as well as the molybdenum content, which creates a desirable Austenite Retention Index, and yet provides improved ultimate tensile strength for the alloy.

These alloys, because they contain nickel and titanium in large quantities, and form the intermetallic compound $Ni_3Ti$ are commonly referred to NiTi elements. It has been found that the NiTi elements produce an ultimate tensile strength of well over 400 ksi, while maintaining high ductility and corrosion resistance.

DETAILED DESCRIPTION OF THE INVENTION

Therefore, in the current alloy improvement program undertaken by the assignee of the invention, a number of five pound sample heats were melted from which the prototype alloy could be tested. Naturally, these heats would be processed under many different conditions, and then tested for estimated ultimate tensile strength, ductility and resistance to corrosion.

After the initial program, it was desired to undergo a program where a small number of the more promising five pound heats would be produced in 100 lb. production runs. After this production run, similar tests were undertaken in order to further refine the product. Finally, an optimal design was chosen, the design being selected for manufacturing purposes.

Table 1 shows the actual chemistries of each of the chemical compositions tested for various performances. The table reports only those elements which by weight had a greater than 0.5% amount as measured in the chemistry;

TABLE 1

| ALLOY NUMBER | Cr | Ni | Ti | Mo | Nb | Ta | W |
|---|---|---|---|---|---|---|---|
| 1 | 11.86 | 7.46 | 1.5 | 4.04 | | | |
| 2 | 11.93 | 6.57 | 0.95 | 4.03 | | | |
| 4 | 11.86 | 6.53 | 1.98 | 4.04 | | | |
| 6 | 11.86 | 8.32 | 1.94 | 4.04 | | | |
| 7 | 11.87 | 8.4 | 0.84 | 4.03 | | | |
| 8 | 11.86 | 7.49 | 1.35 | 2.02 | 0.77 | | |
| 9 | 11.79 | 6.89 | 1.99 | 0 | | | |
| 10 | 11.91 | 7.48 | 1.5 | 0 | | 0.98 | |

TABLE 1-continued

| ALLOY NUMBER | Cr | Ni | Ti | Mo | Nb | Ta | W |
|---|---|---|---|---|---|---|---|
| 12 | 11.92 | 7.52 | 1.49 | 2.01 | | | |
| 13 | 11.92 | 6.65 | 0.98 | 0 | | | |
| 15 | 11.8 | 7.16 | 1.41 | 0 | | | 2.96 |
| 16 | 11.88 | 7.57 | 1.52 | 0 | | | |
| 20 | 11.92 | 7.54 | 1.48 | 2.01 | | 0.98 | |
| 21 | 11.88 | 8.4 | 1.96 | 0 | | | |
| 22 | 11.88 | 7.45 | 1.49 | 2.02 | | | 3.03 |
| 23 | 11.9 | 8.41 | 1 | 0 | | | |
| 24 | 11.78 | 7.51 | 1.91 | 2.03 | 0.78 | | |
| 29 | 12.06 | 6.39 | 2.45 | 5.04 | | | |
| 30 | 11.9 | 8.53 | 2.53 | 4.03 | | | |
| 31 | 11.98 | 8.52 | 2.03 | 5.03 | | | |
| 32 | 11.91 | 8.47 | 2.54 | 5.05 | | | |
| 33 | 11.99 | 13.68 | 2.07 | 4 | | | |
| 34 | 12.01 | 11.8 | 1.98 | 3.98 | | | |

The invention will now be described in relation to the various different processes that went into the formulation of a material to satisfy the above criteria. A general study attempted to narrow the factors before arriving at an alloy program. The study was conducted to determine the total strength of many different alloy chemistries. The goal was to develop chemistries which would surpass strength levels of current alloys. The primary objective was to characterize the effectiveness of each particular alloy addition, and provide a screening tool for future alloy candidates. Ultimately, a comparison of the benefits of strengthening, through alloy heat treatment, with benefits from work hardening during drawing the alloy were explored. Thus, some attention was made to the constraints of needle or wire production.

A number of chemistries were selected to optimize particular alloy additions. Each five pound alloy heat was custom melted. Rods of the alloys were lathe cut to provide four approximate three inch lengths. These lengths of rod were solution treated (annealed) at a prescribed temperature, and afterwards cut to quarter inch length coupons for subsequent processing. Each solution treatment retained one coupon for hardness testing in the annealed state, one coupon for cryogenic treatment, and the remaining coupons for precipitation hardening (aging evaluation).

Ferromagnetism for one coupon was tested at each annealing temperature. This attraction was used to indicate relative amounts of martensite present in the matrix. For any non-ferromagnetic coupons, cryogenic treatment was performed after annealing. This required refrigeration of the coupon for 16 hours, through suspension in liquid nitrogen at $-126.5°$ C. ($-196°$ F.). Ferromagnetic testing was repeated after refrigeration.

Individual sample alloy coupons were treated for annealing purposes at four different temperatures: 1700°, 1800°, 1900° and 2000° F. Solution treatment entailed a one hour anneal followed by water quenching to room temperature. After cutting the coupons, they were precipitation hardened at temperatures between 850° F. and 1125° F. Precipitation hardening entailed a four hour age, followed by air cooling.

Initially, each of these alloy coupons were aged at four different temperatures spanning the precipitation hardening range. Based on the aging response, intermediate temperatures were added until pinpointing a "maximum tensile strength". Tests were conducted with a Rockwell hardness tester using a 150 kg preload and a brale diamond indentor. Rockwell "C" scale hardness readings were converted to approximate ultimate tensile equivalents, using conversions provided by Rockwell.

Test coupon preparation/slicing produced two parallel surfaces by lathe cut. These were slightly hand sanded to remove burrs and machine marks. Five hardness impressions were taken on each coupon—one central reading plus four evenly spaced from the center. We averaged all five measurements, and then ultimate tensile strength was converted from the hardness scale.

Table 2 examines a number of various components. First, through the corresponding alloys from Table 1, it is first determined whether the alloy underwent change from austenite to martensite. In cases where material remained austenitic, this coupon received a greatly abbreviated aging study. Also reported is the optimum tensile strength reached, which is a combination of the response due to anneal strength, and the precipitation hardening response. Accordingly, what remains is a work hardening response which will occur when the material is cold drawn to wire or needle dimensions. Thus, the "delta" response indicates the precipitation hardening response. Also indicated is the annealing strength reached, and temperature used at annealing. Aging temperature is indicated for the precipitation hardening temperature found to be the most desirable for each alloy. Finally, the Austenite Retention Index (ARI) is computed by the following formula:

$$ARI = \%\ Ni + 0.8(\%\ Cr) + 0.6(\%\ Mo) + 0.3(\%\ Co).$$

mum tensile strength was attained at the same temperature as the maximum change in age hardening response.

From these initial bulk tests we drew the following conclusions. First, several chemistries surpass the tensile strength of typical wire grades. Solution treatment alone of these several chemistries provided tensile strengths from 120 ksi to 160 ksi, and was optimized at 1800° F. to 2000° F. Precipitation hardening of the same chemistries reached overall strength from 250 ksi to 300 ksi. Precipitation hardening was found to be most effective for these chemistries in the vicinity of 925° F. All six elements used in the alloys were solid solution hardeners and raised the annealed tensile strength of the alloys. Niobium was particularly effective in this regard.

Titanium, nickel, and tantalum were precipitation hardeners and further increased the response or change in tensile strength through aging Titanium was the most effective in this regard. It was derived that titanium in a range between about 1% and about 2% by weight provided by far the greatest contribution to total heat treat response. Nickel probably responded best at around 2000° F. solution treatment. All NiTi chemistries tested in this run most likely converted to martensite upon quenching to room temperature after solution treatment, except for those alloys which never converted from austenitic. Alloys which did not convert had more than 9.5% nickel. Alloys with less than 9.5% nickel were ferromagnetic and showed heavy magnetic attraction when placed in a magnetic field.

TABLE 2

| ALLOY NUMBER | MAJOR ANNEALED CONSTITUENT MICRO STRUCTURE | OPTIMUM TENSILE REACHED (KSI) | COINCIDENT DELTA RESPONSE (KSI) | ANNEALED STRENGTH REACHED (KSI) | ANNEALING TEMPERATURE USED (F.) | OPTIMUM AGING TEMPERATURE (F.) | ABSTENITE RETENTION INDEX "ARI" (KSI) |
|---|---|---|---|---|---|---|---|
| 1 | MARTENSITE | 262 | 115 | 147 | 1800 | 925 | 19.3 |
| 2 | MARTENSITE | 223 | 84 | 139 | 1700 | 950 | 18.4 |
| 4 | MARTENSITE | 275 | 120 | 155 | 1800 | 925 | 18.4 |
| 6 | MARTENSITE | 292 | 129 | 163 | 1800 | 925 | 20.2 |
| 7 | MARTENSITE | 219 | 91 | 128 | 1800 | 900 | 20.2 |
| 8 | MARTENSITE | 262 | 120 | 142 | 1800 | 925 | 18.5 |
| 9 | MARTENSITE | 256 | 135 | 121 | 1800 | 925 | 16.0 |
| 10 | MARTENSITE | 253 | 129 | 124 | 2000 | 925 | 17.4 |
| 12 | MARTENSITE | 250 | 124 | 126 | 1800 | 900 | 18.1 |
| 13 | MARTENSITE | 204 | 88 | 116 | 1800 | 950 | 16.0 |
| 15 | MARTENSITE | 239 | 109 | 129 | 1700 | 950 | 18.4 |
| 16 | MARTENSITE | 234 | 114 | 120 | 2000 | 925 | 16.9 |
| 20 | MARTENSITE | 267 | 130 | 137 | 2000 | 950 | 18.6 |
| 21 | MARTENSITE | 271 | 145 | 126 | 2000 | 925 | 17.8 |
| 22 | MARTENSITE | 264 | 121 | 143 | 1900 | 925 | 19.6 |
| 23 | MARTENSITE | 219 | 98 | 121 | 2000 | 925 | 17.8 |
| 24 | MARTENSITE | 275 | 135 | 140 | 1900 | 925 | 18.5 |
| 29 | MARTENSITE | 298 | 105 | 193 | 1700 | 900 | 19.0 |
| 30 | MARTENSITE | 305 | 115 | 190 | 2000 | 875 | 20.2 |
| 31 | MARTENSITE | 297 | 133 | 164 | 1900 | 900 | 20.8 |
| 32 | MARTENSITE | 302 | 117 | 185 | 1800 | 900 | 20.8 |
| 33 | AUSTENITE | 89 | 7 | 82 | 1700 | 900 | 25.6 |
| 34 | AUSTENITE | 89 | 2 | 87 | 1700 | 900 | 23.8 |

As can be seen from the tables above, the initial studies in this system all have a nominal chromium composition of 11.9%. This amount is believed sufficient to render good corrosion resistance for stainless steel. Nickel is studied from about 6.5 to 13.7%, optimally between 6.5% and 8.5%. Titanium is studied from 1 to 2.5%. Molybdenum is studied from 0 to 5%. Of secondary importance are the additions of niobium at 0.75%, tantalum at 1%, and tungsten at 3%.

The preceding data was limited to bulk heat treat response, that is, response without a component from work hardening that might otherwise occur from wire drawing. It should be noted that in the bulk test, a maxi- Thus, when drawn to wire, any change in heat treat response was due to strain induced transformations. Of course, reevaluation was recommended of alloy response after cold working these alloys, which was done for the larger heats. In addition, examination of the microstructures may further explain the phases present and different hardening responses in the alloys.

These initial alloys were then subjected to corrosion tests. As a result of these tests, all the above NiTi alloys passed copper sulfate corrosion tests outlined in interim Federal Specification GGS-00816c, incorporated herein by reference. It was found that as a function of the percent chromium or any single alloy addition, the incidence of corrosion did not vary as a function of tensile strength. However, some pitting was noticed during a salt water corrosion test, and it was resolved that this may be related to the amount of ferrite present in the alloys during the martensite phase. Nonetheless, UTS of the alloy at various wire sizes can be determined according to the following formula:

UTS = annealed tensile strength + WHR * ln (change in length final original)

Finally, the last column demonstrates the ultimate tensile strength of the alloys as drawn to wire as 0.022 inches:

TABLE 3

| Alloy Number | Austenite Retention Index (ARI) | Size (Mils) | Annealed TS (ksi) | Length Change (lf/lo) | Work Hardening Rate | As Drawn TS (ksi) | Aging Response | Ultimate TS (ksi) |
| --- | --- | --- | --- | --- | --- | --- | --- | --- |
| 1 | 19.3 | 22 | 147 | 11 | 34 | 229 | 93 | 322 |
| 2 | 18.4 | 22 | 134 | 11 | 30 | 205 | 77 | 282 |
| 4 | 18.4 | 22 | 137 | 11 | 33 | 218 | 105 | 323 |
| 6 | 20.2 | 22 | 147 | 21 | 34 | 254 | 113 | 367 |
| 7 | 20.2 | 22 | 137 | 11 | 24 | 193 | 80 | 273 |
| 8 | 18.5 | 22 | 139 | 11 | 34 | 217 | 82 | 299 |
| 9 | 16 | Broke during drawing | | — | — | — | — | — |
| 10 | 17.4 | 22 | 129 | 21 | 22 | 194 | 101 | 295 |
| 12 | 18.1 | 22 | 132 | 21 | 28 | 218 | 92 | 310 |
| 13 | 16 | 22 | 121 | 21 | 23 | 192 | 59 | 251 |
| 15 | 18.4 | 22 | 132 | 21 | 29 | 217 | 86 | 303 |
| 16 | 16.9 | 22 | 136 | 11 | 17 | 178 | 84 | 262 |
| 20 | 18.6 | 22 | 144 | 21 | 33 | 242 | 96 | 338 |
| 21 | 17.8 | 22 | 122 | 11 | 25 | 183 | 100 | 283 |
| 22 | 19.6 | 22 | 112 | 11 | 23 | 169 | 68 | 237 |
| 23 | 17.8 | 22 | 137 | 11 | 32 | 214 | 95 | 309 |
| 24 | 18.5 | 22 | 138 | 11 | 32 | 216 | 115 | 331 |
| 29 | 19.0 | Broke during drawing | | — | — | — | — | — |
| 30 | 20.2 | Broke during drawing | | — | — | — | — | — |
| 31 | 20.8 | 22 | 161 | 11 | 41 | 260 | 119 | 379 |
| 32 | 20.8 | Broke during drawing | | — | — | — | — | — |
| 33 | 25.6 | 22 | 90 | 11 | 66 | 241 | 62 | 303 |
| 34 | 23.8 | 22 | 96 | 11 | 76 | 269 | 92 | 361 | the alloys viable as needle possibilities were acceptable in both a salt water and a boiling water corrosion test.

Work hardening response for the promising alloys and the aging response of maraged stainless steels drawn into needle wire were then tested. The alloys were received as 0.250 inches round stock. The rod was drawn to wire using one or both of the following flows. In the first flow process, the rod was annealing at 2000° F., swaged to 0.218 inches, further annealed at 2000° F., drawn from 0.218 inches to 0.073 inches. The resulting wire was annealed at at 2000° F. and drawn from 0.073 to 0.022 inches. Alternately, in the second flow process, the rod received as 0.250 inch round was annealed at 2000° F. Then the rod was drawn from 0.250 to 0.101 inches. This wire was annealed at 2000° F. and drawn from 0.101 inches to 0.022 inches.

Tensile tests were then performed. In the anneal condition and as drawn to the following diameters: 0.030 inches, 0.024 inches, 0.022 inches. Further tensile tests were performed on the material when drawn to 0.022 inches and aged as 875° for one hour and then air cooled. In addition, other tensile tests were performed on wires drawn to 0.022 inches and then aged at 950° for one hour and then air cooled.

Table 3 demonstrates the annealed tensile strength as drawn to 0.022 inches and the aging response resulting from the aging of the material. The work hardening rate (WHR) of the alloys was determined by plotting the ultimate tensile strength (UTS) of "as-drawn" wire versus the natural log of the change in length. The slope of the resulting curve is the WHR of the alloy. The Because the availability of material necessitated two different flows, the final anneal of the wire at 2000° F. and drawing the wire from its larger dimensions to an ultimate size of 0.022 inches allows the data to be compared. It is to be noted from the data that the alloys containing increased amounts of molybdenum had a higher work hardening rate, with the aging response virtually unchanged. Also, increasing titanium from 2% to about 2.5% produce an alloy which was brittle and broke in die during the first or second drawing pass.

Because alloys 33 and 34 were high nickel versions of alloy 6, both these alloys were austenitic in the anneal condition, as predicted by their high ARI. These alloys had a low anneal tensile strength, a high initial work hardening rate and yet a lower aging response than our perceived base line alloy, alloy 6.

After the initial promising results, 6 alloys were processed to determine limits of the alloys. Previous work had indicated that alloy 6 had the best combination of properties. It was therefore chosen as a starting point for the second phase of NiTi heats ordered. Thus, alloy 102B is a replicate of alloy 6. Table 4 provides the chemical compositions of the four alloys ultimately studied.

TABLE 4

| Alloy | Cr | Ni | Ti | Mo | Ta |
| --- | --- | --- | --- | --- | --- |
| 101B | 11.48 | 8.35 | 1.40 | 4.04 | 0.90 |
| 102B | 11.48 | 8.27 | 1.88 | 4.06 | none |
| 102C | 11.46 | 8.24 | 1.86 | 4.60 | none |

The purpose of choosing these criteria was to determine the upper limits for the hardening elements titanium, tantalum and molybdenum in the alloy system. Further, the purpose for these choices of alloy was to determine the range of acceptable strand annealing speeds and temperatures for processing NiTi alloys into needle wire. Also, it was desired to provide sufficient material for needle making and age hardening studies.

Three NiTi alloys were then processed. The chemical composition was vacuum induction melted followed by vacuum arc remelting (VIM-VAR). The ingots were forged to about 2.5 inches square, surface ground and hot rolled to about 0.290 inches. The hot rod was annealed at 1500° F., drawn to 0.265 inches, and coil shaved to 0.245 inches.

The shaved wire then was processed into needle wire. First it was precoated and drawn to 0.145 inches. It was then strand annealed at 1940° F. at 3 feet per minute. The material was then drawn from 0.145 inches to 0.093 inches. Then strand annealing was done at temperatures ranging from 1920° F. to 2040° F. at speeds from 3 feet to 24 feet per minute.

TABLE 5

| Annealing Temp. F. | Annealing Speed - feet per minute | | | |
|---|---|---|---|---|
| | 3 | 6 | 12 | 24 |
| Alloy number - 102C | | | | |
| 1920 | cracks @47 | brittle @36 | cracks @41 | brittle @54 |
| 1960 | cracks @47 | cracks @47 | brittle @31 drawn to 21 WHR = 34 | brittle @41 |
| 2000 | drawn to 21 WHR = 28 | cracks @47 drawn to 21 WHR = 29 | drawn to 21 WHR = 31 | cracks @47 |
| 2040 | cracks @47 | cracks @47 | cracks @41 | drawn to 21 |
| Alloy number - 101B | | | | |
| 1920 | | brittle @36 | brittle @54 | brittle @54 |
| 1960 | brittle @36 | cracks @47 brittle @36 | brittle @36 | brittle @41 |
| 2000 | brittle @24 | drawn to 21 WHR = 32 | cracks @46 too short @24 | h |
| 2040 | drawn to 21 WHR = 25 | brittle @31 | cracks @46 drawn to 21 WHR = 31 | brittle @31 |
| Alloy number - 102B | | | | |
| 1920 | too short @24 | brittle @36 | scratched @24 | brittle @54 |
| 1960 | drawn to 15.5 WHR = 28 | drawn to 21 WHR = 35 | cracks @47 | cracks @47 too short @24 |
| 2000 | drawn to 21 WHR = 28 | drawn to 21 WHR = 32 | drawn to 15.5 WHR = 33 | drawn to 21 WHR = 35 |
| 2040 | cracks @47 | drawn to 15.5 WHR = 29 | drawn to 21 WHR = 33 | drawn to 21 WHR = 37 |

The material was then drawn from 0.093 inches to 0.021 inches and then drawn from that size to either 0.018 inches or 0.0155 inches, the applicable sizes for needles.

Tensile testing on drawn wire was used to determine the work hardening rate of the alloys. Results are as follows:

TABLE 6

| ALLOY | ANNEAL TEMP (°F.) | ANNEAL SPEED (fpm) | UTS AS-ANN (ksi) | UTS AS-DRWN to 0.021" (ksi) | UTS AS-DRWN to 0.0155" (ksi) |
|---|---|---|---|---|---|
| 102b | 2040 | 6 | 161 | 248 | 266 |
| | 2040 | 12 | 164 | 248 | |
| | 2040 | 24 | 157 | 264 | |
| | 2000 | 3 | 158 | 245 | |
| | 2000 | 6 | 163 | 252 | |
| | 2000 | 12 | 160 | 263 | 266 |
| | 2000 | 24 | 160 | 254 | |
| | 1960 | 3 | 156 | 240 | 260 |
| | 1960 | 6 | 158 | 257 | |
| 102c | 2000 | 3 | 160 | 256 | |
| | 2000 | 6 | 161 | 252 | |
| | 2000 | 12 | 162 | 257 | |
| | 1960 | 12 | 160 | 263 | |
| 101b | 2000 | 6 | 147 | 243 | |
| | 2040 | 3 | 153 | 235 | |
| | 2040 | 12 | 153 | 237 | |

Some conclusions were made after this round of testing. It was resolved that our alloy 102b was successfully annealed for wire drawing at a wide range of annealing temperatures and speeds. Thus, the chemical composition of alloy 102b, among others, is acceptable for a needle wire. Alloy 101b was highly susceptible to cracking. Thus, it was concluded that the titanium plus tantalum content of alloys for needles should be limited to about 2.1%, especially since increasing titanium from 2.0% to 2.5% caused brittleness. Alloy 102c, with 4.6% molybdenum, was susceptible to cracking and breaking at many of the annealing speeds and temperatures.

Thus, the molybdenum content of the alloys should be limited to about 4.1%.

Alloy 101B, with 1.5% Ti and 1.0% Ta experienced similar ductility to Alloy 30, with 2.5% Ti during drawing. Our conclusion, therefore, was that the alloy additions of tantalum have an equal effect on ductility as titanium. Alloys 10 and 20, which had 1.5% Ti and 1.0% Ta, but at Mo contents of 0 and 2% respectively showed both good ductility and good final strength. In other words, titanium and combined tantalum behave similarly in our alloy, and therefore their maximum amounts should be kept below about 2.1%. It is to be noted that this combination at 2.5% was brittle in our alloy.

As a last function of this stage, ten of the chosen alloys were tested for bend test strength. Each alloy was aged at temperatures between 775° F. and 1075° F. for timed intervals between 1 hour and 23 hours, and air cooled. Bend tests were conducted and maximum bend strength and total annular deflection for ductility were recorded. Conversion to ultimate tensile strength was accomplished mathematically, using established conversion tables. All bend tests were conducted to 84° deflection using a moment arm of 0.150", and calibration to one pound full scale load.

As seen from the tables, alloy 34 produced a very high tensile strength and heat treat response matched only by alloy 33. In contrast, their ductility was also lowest. Both these alloys contained high nickel, resulting in a high ARI, and were austenitic as annealed. Due to extensive cold work during wire drawing, there was strain induced transformation to martensite. Information provided during wire drawing indicates that alloy 34 transformed fully to martensite and alloy 33 has largely transformed. The remaining alloys tested were essentially martensitic as annealed, and passed the ductility tests:

strengths were grouped at about 300 ksi for all these alloys. These strengths surpass all the earlier chemistries. As a conclusion of these second stage tests, it was reaffirmed that the limit of solid solubility for the combination of titanium and tantalum should be at a maximum between about 2.1 and about 2.3%, and nickel was determined from these studies to be most beneficial at a maximum between 8% and 9.5%.

Finally, needle wire from heat 102b (the most desirable heat) was processed into needles using standard needle making equipment, tooling and processes. Tensile strength of the needle wire was higher than normal for typical alloys. Channel forming studies were also conducted to determine if channels could be punched in the higher strength material. The needles were compared with present needles made before or after these heat 102b needles.

In conclusion, it was determined that this heat can be successfully processed into needles without major equipment or tooling modifications. Bend strength of the needles made from heat 102b was 20% to about 28% higher than typical needles made of the same type. This compared favorably with the high calculated tensile strength.

Therefore, in conclusion, these heats when drawn to needle sizes produced ultimate tensile strengths well above 400 ksi. In this regard, it was determined from our studies that such an alloy is highly desirable in use as wire or especially in use as needles.

Therefore, with the above tests, it has been determined that new subject matter exists in condition for a patent and it is intended that the following claims and their equivalents delineate the scope of that patent.

What is claimed is:

1. A martensitic stainless steel alloy comprised of about 11½% to about 12½% chromium by weight, between about 6.3% and about 9.5% nickel by weight,

TABLE 7

| ALLOY NUMBER | CHEMISTRY | | | | ARI (calculated) | DIAMETER (mils) | BEND STRENGTH (in-lb) × 100 | TENSILE STRENGTH calculated (ksi) | DUCTILITY (degrees) |
|---|---|---|---|---|---|---|---|---|---|
| | NICKEL: (percent) | MOLY: (percent) | TITANIUM: (percent) | OTHER: | | | | | |
| 1 | 7.3 | 4 | 2 | | 19.3 | 11.5 | 8.75 | 350 | 84 |
| 102A | 8.3 | 3.5 | 1.5 | | 19.9 | 11.5 | 7.41 | 296 | 84 |
| 7 | 8.3 | 4 | 1 | | 20.2 | 11.5 | 7.55 | 302 | 84 |
| 102B | 8.3 | 4 | 2 | | 20.3 | 11.5 | 10.02 | 401 | 84 |
| 102C | 8.3 | 4.5 | 2 | | 20.6 | 11.5 | 9.62 | 385 | 41 |
| 101B | 8.3 | 4 | 1.5 | Tant 1 | 20.8 | 11.5 | 10.01 | 400 | 84 |
| 103A | 10.5 | 4 | 2 | | 22.4 | 15.5 | 27.20 | 419 | 68 |
| 34 | 11.9 | 4 | 2 | | 23.8 | 11.5 | 10.98 | 439 | 26 |
| 103C | 13 | 4 | 2 | | 24.9 | 15.5 | 26.00 | 400 | 65 |
| 33 | 13.7 | 4 | 2 | | 25.6 | 11.5 | 10.47 | 419 | 38 |

In general, from these ductility tests, the higher the nickel content, the greater the precipitation hardening obtained. But along with optimal age hardening came degraded ductility. In contrast, none of the martensitic alloys showed appreciable ductility loss.

Speed of response indicated that one to two hours is sufficient to produce 90% or more of the precipitation hardening. The best combination of strength and ductility among these eight alloys was therefore found at the martensitic alloy 102b. A calculated tensile strength of 400 ksi was achieved with heat treat response of 120 ksi. Ductility surpassed full deflection in the bend test under which we proceeded.

With these new NiTi alloys chosen to evaluate high titanium levels (2% and greater), and molybdenum levels at 4% or greater, resulting optimum tensile molybdenum about 3% to 4%, and the combination of titanium and tantalum ranging from about 1.5% to about 2.4%, with the remainder comprising iron and trace elements, containing less than about 0.1% carbon.

2. The alloy of claim 1 wherein the amount of molybdenum is between 3.5% and 4%.

3. The alloy of claim 1 wherein the combination of titanium and tantalum is no higher than about 2.1%.

4. The alloy of claim 3 wherein the amount of nickel is between 7.5% and 8.5%.

5. The alloy of claim 3 wherein the amount of titanium is about 2.1%.

6. The alloy of claim 3 of the amount of tantalum is about 1.5%.

7. The alloy of claim 3 wherein the amount of chromium is about 12%.

8. The alloy of claim 7 wherein the amount of titanium is about 2.1%.

9. The alloy of claim 8 wherein the alloy is used in the manufacture of surgical needles.

10. The alloy of claim 8 wherein the Austenite Retention Index is between about 17.3% to about 21.4%.

11. A needle formed from martensitic stainless steel alloy comprised of about 11½% to about 12½% chromium by weight, between 6.3% and about 9.5% nickel by weight, molybdenum about 3% to 4%, and the combination of titanium and tantalum ranging from about 1.5% to about 2.4%, with the remainder comprising iron and trace elements, containing less than about 0.1% carbon.

12. The needle of claim 11 wherein the amount of molybdenum is between 3.5% and 4%.

13. The needle of claim 11 wherein the combination of titanium and tantalum is no higher than about 2.1%.

14. The needle of claim 11 wherein the amount of nickel is between 7.5% and 8.5%.

15. The needle of claim 14 wherein the amount of titanium is about 2.1%.

16. The needle of claim 14 of the amount of tantalum is about 1.5%.

17. The needle of claim 14 wherein the amount of chromium is about 12%.

18. The needle of claim 17 wherein the amount of titanium is about 2.1%.

19. The needle of claim 18 wherein the Austenite Retention Index is between about 17.3% to about 21.4%.

20. A maraged stainless steel alloy comprised of about 11½% to about 12½% chromium by weight, between about 6.3% and about 9.5% nickel by weight, molybdenum between about 3% and 4%, titanium about 2.1% by weight, with the remainder comprising iron and trace elements.

21. The alloy of claim 20 wherein the amount of titanium is substituted by tantalum at about 1.5%.

22. The alloy of claim 20 wherein the amount of molybdenum is between about 3.5% and 4%.

23. The alloy of claim 22 wherein the amount of nickel is between 7.5% and 8.5%.

24. The alloy of claim 22 wherein the amount of chromium is about 12%.

25. The alloy of claim 22 wherein the amount of carbon is less than 0.1%.

26. The alloy of claim 22 wherein the alloy is used in the manufacture of surgical needles.

* * * * *